(12) United States Patent
Cavazza et al.

(10) Patent No.: US 6,348,495 B1
(45) Date of Patent: Feb. 19, 2002

(54) METHOD FOR TREATING CELIAC DISEASE

(75) Inventors: Claudio Cavazza; Luigi Mosconi, both of Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 09/626,151

(22) Filed: Jul. 26, 2000

Related U.S. Application Data

(60) Continuation-in-part of application No. 09/441,328, filed on Nov. 16, 1999, now Pat. No. 6,143,785, which is a division of application No. 08/868,627, filed on Jun. 4, 1997, now Pat. No. 6,013,607.

(30) Foreign Application Priority Data

Jun. 6, 1996 (IT) ........................................ RM96A0396

(51) Int. Cl.⁷ ..................... A61K 31/205; A61K 31/225
(52) U.S. Cl. .......................... 514/547; 514/556; 514/642
(58) Field of Search ................................. 514/642, 547, 514/556

(56) References Cited

U.S. PATENT DOCUMENTS 4,958,418 A  9/1990  Dufour ...................... 24/713.6

FOREIGN PATENT DOCUMENTS

| JP | 1-156927 | 6/1989 |
| WO | WO 97/272177 | 7/1997 |
| WO | WO 99/56698 | 11/1999 |

OTHER PUBLICATIONS

Lerner et al, Gut (1993) 34,933–935 Serum carnitine concentrations in coeliac disease.
Ceccarelli et al Minerva Pediatrica (1992) vol. 44, No. 9, 401–405 Concentrazioni plasmatiche di L–carnitine in bambini celiaci.
English translation Italian patent appln. RM 96A 00396 filed Jun. 6, 1996.

*Primary Examiner*—Theodore J. Criares
*Assistant Examiner*—Jennifer Kim
(74) *Attorney, Agent, or Firm*—Nixon & Vanderhye

(57) ABSTRACT

A method for treating celiac disease comprising administration of a composition containing an alkanoyl L-carnitine wherein the alkanoyl group is straight or branched and has 2–6 carbon atoms and the pharmacologically acceptable salts thereof.

20 Claims, No Drawings

METHOD FOR TREATING CELIAC DISEASE

CROSS-REFERENCE TO RELATED APPLICATIONS

This application is a continuation-in-part of earlier application Ser. No. 09/441,328 filed Nov. 16, 1999, now U.S. Pat. No. 6,143,785, which is a division of Ser. No. 08/868,627 filed Jun. 4, 1997, now U.S. Pat. No. 6,013,607.

The present invention relates to a new therapeutic use of the lower alkanoyl L-carnitines and their pharmacologically acceptable salts to produce pharmaceutical compositions for the treatment of chronic intestinal disorders, in particular inflammatory bowel diseases, more particularly, ulcerative colitis or celiac disease.

The present invention also relates to pharmaceutical compositions suitable for rectal administration, particularly in the form of foams or enemas, containing the above-mentioned alkanoyl L-carnitines.

Ulcerative colitis is an inflammatory, ulcerative disease of the colon of unknown aetiology, very often characterised by haematic diarrhoea.

It usually originates in the recto-sigmoid area, from which it may spread proximally with possible involvement of the entire colon. Alternatively, it may attack a substantial portion of the large bowel right from the outset.

The complications of ulcerative colitis are particularly severe: it has been documented, in fact, that there is an enormous increase in the risk of colon cancer in patients suffering from ulcerative colitis. The incidence of colon cancer increases with both involvement of the entire colon and with a duration of disease exceeding 10 years.

In both the mild-to-moderate forms and the moderately or distinctly severe forms of the disease, corticosteroids constitute the drugs of choice, namely hydrocortisone, betamethasone and prednisone.

In the mild-to-moderate forms, physiological solution containing hydrocortisone is administered via an enema which is retained in the bowel as long as possible.

In the moderately severe forms, systemic corticosteroid therapy is necessary, consisting generally in 10–15 mg of prednisone t.i.d. or q.i.d. per os, which is capable of inducing drastic remission.

In the more severe forms requiring admission to hospital, the corticosteroid therapy is administered parenterally.

Both the systemic and topical administration of these drugs gives rise to serious side effects, mainly related to interference with the hypothalamo-pituitary-adrenal axis.

The side effects due to topical treatment of ulcerative colitis with these traditional corticosteroids are, far instance, transient or prolonged depression of adrenocortical function, weight gain, acne and moon face.

Though it is well known, particularly in the moderately severe forms of the disease, that the daily corticosteroid dose can be gradually reduced to 10–20 mg per week after 1–2 weeks of treatment, even such low corticosteroid doses continue to induce harmful side effects, the elimination or at least the drastic reduction of which constitutes a therapeutic goal of primary importance.

Celiac disease (or celiac syndrome) is a chronic intestinal disorder caused by a specific intolerance to gluten present in wheat, rye, barley and oats proteins included in the diet leading to dramatic changes in the small intestinal mucosa and subsequent impaired absorption. The celiac syndrome can affect genetically susceptible subjects (around 3‰). Symptoms comprise diarrhoea and other malabsorption symptoms, including total atrophy of intestinal mucosa.

It is known that in humans said pathologic alterations are produced by the action on the intestinal mucosa of digestion products of wheat gluten and, in particular, by the 70% ethanol soluble gluten protein fraction. Said protein fraction, generally name as "prolamin" (in wheat, in particular, it is named as "gliadin"), is present in several cereals in different proportions and is composed of numerous proteins with different molecular weights, and having an high glutamine (one glutamine residue every three amino acids) and proline (a proline residue every seven amino acids) content, and a low ionic strength (due to few residues able to ionise in solution).

Current treatment is effected by a well balanced gluten-gliadin-free diet high in calories and proteins and normal in fat. This excludes cereal grains with the exception of rice and corn. Patients affected by celiac disease not responding to gluten-gliadin-free diet are treated with glucocorticoid steroids. For example U.S. Pat. No. 4,958,418, assigned to Glaxo Group Limited, teaches the use of fluticasone dipropionate, an anti-inflammatory steroid, This patent clearly establishes that celiac disease, ulcerative colitis and Crohn's disease are all embedded in the category of bowel diseases which respond to treatment of glucocorticoid steroids.

Based on the study of toxic peptides obtained by different prolamins, WO 97/27217, in the name of Istituto Superiore di Sanita, provides a protein compound having a sequence comprised in the proteins of durum wheat and being not toxic for celiac subjects, in particular a protein of the following sequence: QQPQDAVQPF.

WO 99/56698, in the name of Copenhagen University, discloses a method for treating celiac disease comprising interfering with the deamidation of at least one glutamine residue in a gliadin molecule. Practically, the treatment comprises administering to a patient suffering from celiac syndrome at least one of the following substances: a) a substance capable of increasing the pH in the gastroduodenal tract, e.g. an antacid, an anticholinergic agent, H2-receptor antagonists or a proton pump inhibitor, b) an antibiotic or antimicrobial agent acting against deamidating bacteria and/or a substance capable of interfering with deamidating enzymes. In a wide sense, a method for treating celiac disease is prospected in JP 1156927, to University Leland Stanford, by administering an antagonist to IFN-$_{65}$.

There is still a strong need to make available a method for the treatment of celiac disease using a simple therapeutic scheme, with an easily managed drugs, with low or null side effects. The cost of the drug is also important.

Celiac patients, children in particular, proved to have low serum L-carnitine levels, most likely due to the damaged bowel mucosa (Lerner A. et al., Gut; 34: 933–935; Ceccarelli M. et al. Minerva Pediatr. 1992; 44:401–5). Indeed, celiac patients do, not absorb hexogenous L-carnitine. From a clinical point of view, L-carnitine deficiency cannot be associated to celiac disease. To date, it has never been demonstrated that L-carnitine deficiency may give celiac disease.

Therefore, it was totally unexpected to find that an alkanoyl L-carnitine is effective in the treatment of celiac disease according to is the teaching of the present invention. The object of the present invention is to provide a method for treating and pharmaceutical compositions useful for the treatment of chronic intestinal disorders, in particular inflammatory bowel diseases, more particularly, ulcerative colitis or celiac disease. The aim of the present invention is to provide compositions and methods for the treatment of the above disease, which, while affording equivalent therapeutic benefit, make it possible to use a lower daily dose of corticosteroid drug, with a consequent distinct reduction in the side effects induced by such drugs.

A further object of the present invention is to provide a composition of the above-mentioned type which enables complete remission of symptoms to be achieved and which lends itself to oral or, if necessary, to rectal administration, in the form of a foam or enema, thus making it possible to avoid corticosteroid administration via the parenteral route even in the most severe cases.

These objects are achieved according to the present invention by means of the use of lower alkanoyl L-carnitines in which the alkanoyl group, straight or branched, has 2–6 carbon atoms and of their pharmacologically acceptable salts to produce the aforementioned compositions. The preferred alkanoyl L-carnitines are acetyl, propionyl, butyryl, isabutyryl, valeryl and isovaleryl L-carnitine. Propionyl L-carnitine, butyryl L-carnitine and their pharmacologically acceptable salts are particularly preferred.

What is meant by a pharmacologically acceptable salt of an alkanoyl L-carnitine is any salt of the latter with an acid which does not give rise to unwanted toxic or side effects. These acids are well known to pharmacologists and pharmacy experts.

Non-limiting examples of such salts are, for instance, chloride, bromide, orotate, acid aspartate, acid citrate, acid phosphate, fumarate and acid fumarate, lactate, maleate and acid maleate, acid oxalate, acid sulphate, glucose phosphate, tartrate and acid tartrate.

Though, according to the present invention, the alkanoyl L-carnitine and the reduced dose of corticosteroid can be administered orally, it might be necessary that the preferred alkanoyl L-carnitine administration route is rectal. In particular, those forms of rectal administration, such as foams and enemas, are preferred, which allow prolonged contact between the alkanoyl L-carnitine and the intestinal tract affected by the inflammatory ulcerative disease.

The preparation of these foams and enemas and the choice of appropriate vehicles and excipients are well known to pharmacy experts.

These compositions capable of being administered by the rectal route may contain additional active ingredients such as anti-diarrhoea agents, antibiotics, anaesthetics, stool softeners and lubricants.

For example, an enema composition comprises from approximately 3 to approximately 15 grams, preferably 6–12 grams, of alkanoyl L-carnitine and possibly 400–600 mg of hydrocortisone or 20–50 mg of prednisone per litre of physiological solution.

Though the daily dose will depend, according to the judgement of the primary care physician, on the subjects weight, age and general condition, it is generally advisable to administer 1–4 g/day—preferably 2–3 g/day—of alkanoyl L-carnitine or a stoichiometrically equivalent amount of one of its pharmacologically acceptable salts. In the preferred rectal administration form, an enema of 500 mL physiological solution containing 5–10 g of alkanoyl L-carnitine—e.g. 6 g of propionyl L-carnitine—is administered twice daily.

Larger doses can safely be administered in view of the substantial non-toxicity of the alkanoyl L-carnitines.

In the embodiment relating to the treatment of celiac disease, the alkanoyl L-carnitine, among which propionyl L-carnitine is preferred, may be used alone or in combination with at least one active agent used in the treatment of celiac disease. Active agents for the treatment of celiac disease are well-known in the art and the skilled person will be able to determine the suitable agent. Glucocorticoids, such as hydrocortisone, prednisone or prednisolone may be used as well as other active agents. Preferably, the method according to the present invention is associated with the proper gluten-free diet.

In a further embodiment of the invention, the alkanoyl L-carnitines, and in the particularly preferred embodiment, propionyl L-carnitine, are combined with short chain fatty acids. The latter are used in celiac disease therapy. It is important that the alkanoyl L-carnitine and the short chain fatty acid be combined in a physical form and not bound in a chemical entity (such as, for example an ester). Though the inventors do not wish to be bound to any theory, it is believed that alkanoyl L-carnitines exert a protective effect toward the cells against potential damaging effects of short chain fatty acids.

In a still further embodiment of the invention, the alkanoyl L-carnitines, and in the particularly preferred embodiment, propionyl L-carnitine, are combined with amino acids, preferably glutamine. The latter are used in celiac disease therapy, where they exert a protective effect towards intestinal epitelial cells.

Details are given here below of clinical studies demonstrating the activity of the compounds according to the invention.

EXAMPLE 1
Rectocolitis Treatment

Three male patients suffering from ulcerative rectocolitis diagnosed by endoscopy and histological examination of biopsy samples, with a BMI (Body Mass Index) of 25 Kg/m and a DCAI (Crohn's Disease Activity Index) of approximately 180 (Gastroenterology 70: 439–444,1976; Vol. 70, no. 3), on treatment with steroids (prednisone 0.20 mg/Kg/day) were treated twice daily for 2 months with an enema containing 6 g of propionyl L-carnitine dissolved in 500 ml of physiological solution.

After only one week's treatment an improvement in the clinical picture was already noticeable with a reduction in the number of daily bowel movements and an improvement in the consistency of the faeces, as well as reduced losses of blood and mucus.

Later in the course of therapy, the subjective symptoms and the objective clinical findings continued to improve with reduction of the CDAI to approximately 120 by the end of the second month.

Thanks to this improvement the patients were able to reduce their cortisone therapy to approximately 0.8 mg/Kg/day.

The endoscopic investigation showed a distinct improvement of the ulcerative lesions with areas of re-epithelialisation and non-friable mucosa on contact with the instrument.

The histological examination revealed a distinct reduction of the inflammation.

No side effects were observed, and patient compliance was optimal.

The results obtained show that by the end of the course of treatment the use of propionyl L-carnitine had significantly reduced (by about 40%) the amount of steroid dug administered to the patients, thus leading to a substantial reduction in its side effects.

EXAMPLE 2

Celiac Disease Treatment

S.C., female, 36 years old, height 168 cm, weight 46 Kg. Regularly born, she was breast-fed by her mother. She had a regular growth, with the common exanthematic diseases typical of young age. Sexual development was normal (menarche at 11 and regular cycle). Two pregnancies, the latter ended at 7 months and half. Celiac disease was suspected in April 1998. First symptoms, diarrhoea and meteorism, appeared on January 1998, followed by anorexia, slimming (about 7.5 Kg), asthenia and dyspepsia. Blood withdrawals and biopsy confirmed the diagnosis. She started free-gluten diet, and, after one month, after diarrhoea disappearance, propionyl L-carnitina was given (2 grams/day orally for two months). At the end of the dietary and pharmacological treatment the complete normalisation of biochemical parameters and clinical symptomatology was observed.

O.A., female, 56 years old, height 165 cm, weight 49 Kg. Regularly born, she was breast-fed by her mother for about 1 year. Sexual development was normal (menarche at 14 and regular cycle). Two pregnancies (1 male and 1 female) and one abortion before diagnosis. She entered menopausal period at 51. In 1976 important diarrhoea appeared (10–15 discharges/day) together with weight decrease of about 10 Kg. Routine investigations ended in 1979, with a diagnosis of celiac disease (histology: complete atrophy of intestinal villi, flat profile, infiltration of lymphocytes and plasmacells in the tunica). The patient started gluten-free diet for six months with disappearance of symptoms. Subsequently, she alternated gluten-free products with normal ones until February 1997, when hyposiderhaemia, asthenia, meteorism and diarrhoea appeared (about 10 discharges/day, liquid faeces). Diagnosis was reconfirmed. From that time, the patient is under rigid diet and had a weight gain of 7 Kg with partial correction of anaemia. Since the patient did not tolerate intravenous iron administration, normalisation of biochemical parameters required a longer time. Propionyl L-carnitine was given (2 grams/day orally for two months), with an improvement of the general symptomatology.

N.S., female, 26 years old, height 160 cm, weight 42 Kg. Pre-term born (8 months), she was breast-fed by her mother for about 1 year. At 3, diagnosis of celiac disease was ascertained. From 3 to 7, she was given a gluten-free diet, later interrupted on suggestion of the care physician, who considered her recovered. Menarche at 12 and cycle regular as to frequency, but irregular as to duration. Two pregnancies (1 male and 1 female, both of them affected by celiac disease), one of the pre-term of 8 months. After the second birth (1992) symptoms appeared again (abdominal pains, anorexia, weight decrease of about 12 Kg, asthenia, meteorism and anaemia). In November 1997, diagnosis was reconfirmed. From that time, the patient is under diet and started the treatment with propionyl L-carnitine (2 grams/day orally for two months), with an improvement of the general symptomatology.

S.C., male, 20 years old, height 178 cm, weight 69 Kg. Regularly born, she was breast-fed by her mother for about 40 days. At about 9 months diarrhoea and meteorism appeared, lasting one month. Regular growth and sexual development. Measles. In 1995 a blister dermatitis appeared, with strong itching. After different hypotheses, a Duhring dermatitis was diagnosed. An EGDS was carried out with biopsies reporting celiac disease. A rigid gluten-free diet started. Dermatitis was resolved, but still 2–3 daily discharges, with poorly formed faeces and abdominal pains were reported. The patient started the treatment with propionyl L-carnitine (2 grams/day orally for two months), with an improvement of the general symptomatology. After 4 months the patient started sporting activity again.

C.L., female, 51 years old, height 158 cm, weight 55 Kg. Regularly born, she knew nothing about breast-feeding. Regular growth. Menarche at 13 and cycle generally regular. Now she is near menopausal period, Three regularly-termed pregnancies and two spontaneous abortions at three months. In may 1996, haematic diarrhoea appeared, together with abdominal pains, weight decrease of about 10 Kg, meteorism, sideropenic anaemia, asthenia and muscular cramps. In May 1997, she was sent to hospital for resection of a polypus from the sigmoid flexure. In this occasion, diagnosis of celiac disease was ascertained. A rigid diet was followed for 6 months, then irregularly. A gluten-free diet was started again and the treatment with propionyl L-carnitine started (2 grams/day orally for two months), with an improvement of the general symptomatology.

C.E., female, 30 years old, height 178 cm, weight 62 Kg. Regularly born, she was breast-fed by her mother for some months. Regular growth. Menarche at 13 and cycle always regular. The first symptoms, suggesting celiac disease, appeared in December 1997. Other than anaemia (present since 16), abdominal pains, meteorism, asthenia and depression were present. EGDS and blood analysis confirmed the diagnosis. The diet was started and, after 4 months, since general discomfort persisted, she was treated with propionyl L-carnitine (2 grams/day orally for three months), with an improvement of the general symptomatology.

C.M., female, 38 years old, height 164 cm, weight 52 Kg. Regularly born, she was breast-fed by her mother for 9 months. Regular growth and sexual development. Menarche at 12 and irregular cycle only during her teens. She always suffered a marked asthenia, poor school results and irritability. Anaemia started in 1987. In March 1996 arthritis at left knee was ascertained and she resulted positive for thyroid-specific antibodies. In January 1999, celiac disease was ascertained. Together with diet, propionyl L-carnitine (2 grams/day orally for four months) was given, with an improvement of the general symptomatology.

What is claimed is:

1. A method of treating celiac disease comprising administration of a composition containing an alkanoyl L-carnitine wherein the alkanoyl group is straight or branched and has 2–6 carbon atoms or a pharmacologically acceptable salt thereof.

2. A method of claim 1, wherein the alkanoyl L-carnitine is selected from the group consisting of acetyl, propionyl, butyryl, isobutyryl, valeryl and isovaleryl L-carnitine.

3. A method of claim 1, wherein administration is selected from the group consisting of oral, parenteral and rectal route.

4. A method of claim 3, wherein said route is oral.

5. A method of claim 1, wherein said composition further comprises at least one active agent used for the treatment of celiac disease.

6. A method of claim 5, wherein said active agent is a corticosteroid having an anti-inflammatory action.

7. A method of claim 6, wherein said corticosteroid is selected from the group consisting of hydrocortisone, betamethasone, prednisone, prednisolone and fluticasone.

8. A method of claim 5, wherein said active agent is a short chain fatty acid.

9. A method of claim 5, wherein said active agent is an amino acid.

10. A method of claim 9, wherein said amino acid is glutamine.

11. A method of claim 3, wherein said route is rectal.

12. A method of claim 11, wherein in said rectal route, said composition further comprises at least one active agent used for the treatment of celiac disease.

13. A method of claim 12, wherein said active agent is a corticosteroid having an anti-inflammatory action.

14. A method of claim 13, wherein said corticosteroid is selected from the group consisting of hydrocortisone, betamethasone, prednisone, prednisolone and fluticasone.

15. A method of claim 12, wherein in said rectal route, said active agent is a short chain fatty acid.

16. A method of claim 12, wherein in said rectal route, said active agent is an amino acid.

17. A method of claim 16, wherein in said rectal route, said said amino acid is glutamine.

18. A method of claim 11, wherein in said rectal route, said composition is in the form of foam or enema, said foam or enema further comprising a compound selected from the group consisting of an anti-diarrhoea agent, antibiotic, anaesthetic, stool softener and a lubricant.

19. A method of claim 12, wherein in said rectal route, said composition is in the form of foam or enema, said foam or enema further comprising a compound selected from the group consisting of an anti-diarrhoea agent, antibiotic, anaesthetic, stool softener and a lubricant.

20. A method of claim 1 wherein said pharmacologically acceptable salt of alkanoyl L-carnitine is selected from chloride, bromide, orotate, acid aspartate, acid citrate, acid phosphate, fumarate and acid fumarate, lactate, maleate and acid maleate, acid oxalate, acid sulphate, glucose phosphate, tartrate and acid tartrate.

* * * * *